United States Patent
Koopman

(10) Patent No.: US 7,972,312 B2
(45) Date of Patent: Jul. 5, 2011

(54) COMPAC SYRINGE

(76) Inventor: Robert A. Koopman, Roscoe, IL (US)

( * ) Notice: Subject to any disclaimer, the term of this patent is extended or adjusted under 35 U.S.C. 154(b) by 967 days.

(21) Appl. No.: 11/103,236

(22) Filed: Apr. 11, 2005

(65) Prior Publication Data

US 2006/0229568 A1 Oct. 12, 2006

(51) Int. Cl.
*A61M 5/00* (2006.01)

(52) U.S. Cl. ........ 604/187; 604/181; 604/192; 128/919; 600/432

(58) Field of Classification Search ........... 604/68–72, 604/82–92, 181–243; 128/919; 600/431–432; 606/1, 167
See application file for complete search history.

(56) References Cited

U.S. PATENT DOCUMENTS

| | | | | |
|---|---|---|---|---|
| 1,678,991 A | * | 7/1928 | Marschalek | 604/220 |
| 3,506,008 A | * | 4/1970 | Huck | 604/193 |
| 3,642,000 A | * | 2/1972 | Baker | 604/218 |
| 3,786,811 A | | 1/1974 | Holbrook | |
| 4,298,036 A | * | 11/1981 | Horvath | 141/1 |
| 4,581,023 A | * | 4/1986 | Kuntz | 604/234 |
| 5,935,104 A | * | 8/1999 | Janek et al. | 604/110 |
| 6,595,961 B2 | * | 7/2003 | Hetzler et al. | 604/181 |
| 7,074,207 B2 | * | 7/2006 | Yang | 604/110 |
| 2003/0083621 A1 | * | 5/2003 | Shaw et al. | 604/164.07 |
| 2004/0010238 A1 | * | 1/2004 | Manera et al. | 604/289 |

FOREIGN PATENT DOCUMENTS

WO WO89/08468 * 8/1989

* cited by examiner

*Primary Examiner* — Nicholas D Lucchesi
*Assistant Examiner* — Quynh-Nhu H Vu
(74) *Attorney, Agent, or Firm* — Gavrilovich, Dodd + Lindsey LLP

(57) ABSTRACT

A compact syringe comprises a cylindrical barrel, a stopper movable within the barrel and a detachable clip-on plunger. The plunger has a resilient c-shaped shaft for clipping onto the barrel's exterior when the syringe is not in use. When in use, the plunger is removed from the barrel and its c-shaped shaft is compressed slightly and then inserted into the rear end of the barrel to apply movement force to the stopper. The clip-on plunger reduces the amount of storage space required by the compact syringe. Reducing syringe storage space is of particular importance for disposable, single-use syringes.

19 Claims, 2 Drawing Sheets

COMPAC SYRINGE

TECHNICAL FIELD

The invention relates generally to syringes, and more specifically, to a new and improved compact syringe having a reduced length profile when not in use.

BACKGROUND

Many different types of syringes have been devised for delivering and injecting medicines. Pre-packaged, disposable syringes are now widely used because they are reliably hygienic, precisely dosed and generally more cost effective than traditional re-usable syringes.

Required storage space is an important feature of pre-packaged syringes. Smaller syringes are not only less expensive to ship, but they are also less expensive to store in inventory. This is especially important in hospitals and pharmacies, where storage space for medicines and medical devices is at a premium. This is even more important in pharmacies and hospitals that use automated prescription drug dispensers that robotically retrieve medicines from stored inventory, such as a Pyxis® dispenser system from CardinalHealth, Inc. In these systems, operational costs are directly related to the storage space required per dose. Thus, in these automated systems, reducing the storage space required by prescription drugs can reduce the cost of providing medicines to patients, and therefore, there is great incentive to minimize the physical size of disposable syringes dispensed through these systems.

Current syringe designs do not squarely address the increasingly important need for a low-cost syringe having reduced storage space requirements. Thus, an improved syringe embodying a design that reduces storage space is needed.

SUMMARY

It is an advantage of the invention to provide a novel compact syringe that reduces storage space requirements by eliminating the usual rearwardly extending plunger of the syringe, while the syringe is in its packaged, pre-use state. This substantially reduces the physical length of the stored syringe.

According to one embodiment of the invention, instead of a plunger extending from the syringe's rear end, a "clip-on" plunger is attached around the syringe's barrel during pre-packaging. In use, the clip-on plunger is removed from the syringe barrel and inserted into the syringe's rear end to express the contents of the syringe in the usual manner. The use of the clip-on plunger dramatically reduces the storage space required by the syringe.

Other aspects, features, embodiments, processes and advantages of the invention will be or will become apparent to one with skill in the art upon examination of the following figures and detailed description. It is intended that all such additional features, embodiments, processes and advantages be included within this description, be within the scope of the invention, and be protected by the accompanying claims.

BRIEF DESCRIPTION OF THE DRAWINGS

It is to be understood that the drawings are solely for purpose of illustration and do not define the limits of the invention. Furthermore, the components in the figures are not necessarily to scale, emphasis instead being placed upon illustrating the principles of the invention. In the figures, like reference numerals designate corresponding parts throughout the different views.

DETAILED DESCRIPTION

The following detailed description, which references to and incorporates the drawings, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1:
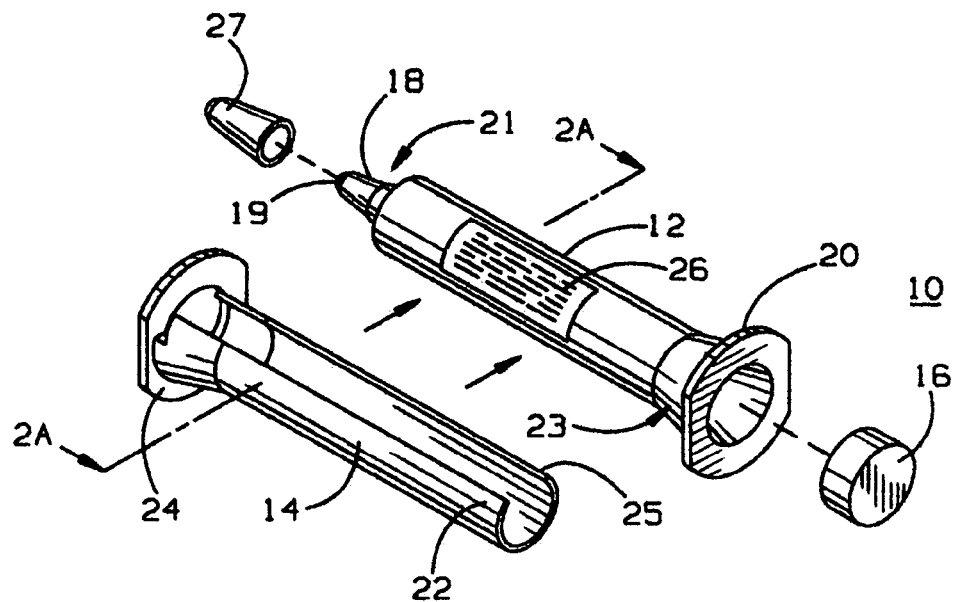
FIG. 1 is an exploded perspective view of a syringe having a clip-on plunger in accordance with an exemplary embodiment of the invention.

Turning now to the drawings, and in particular to FIG. 1, there is shown an exploded perspective view of a compact oral syringe 10 in accordance with an exemplary embodiment of the invention. This embodiment is particularly suited for use as a single-use (i.e., disposable) syringe for administering oral medications.

Figure 4:
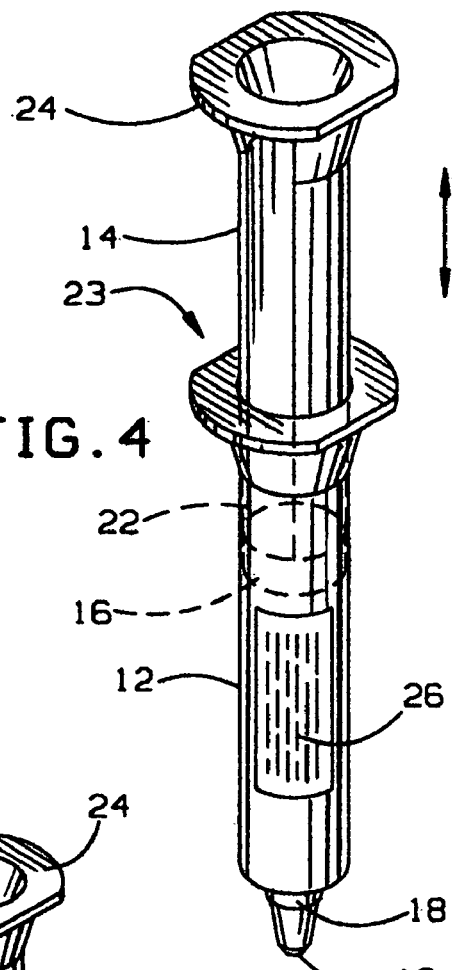
FIG. 4 is a perspective view of the syringe of FIG. 1 during use.

The compact syringe 10 comprises a cylindrical barrel 12, a stopper 16 movable within the barrel 12 and a detachable clip-on plunger 14. The plunger 14 has a resilient c-shaped shaft 22 for clipping onto the barrel's exterior when the syringe 10 is not in use. When in use, the plunger 14 is removed from the barrel 12 (as shown in FIG. 1) and its c-shaped shaft 22 is compressed slightly in an inward radial direction and then inserted into the rear end 23 of the barrel 12 (as shown in FIG. 4) to apply movement force to the stopper 16.

Figure 6:
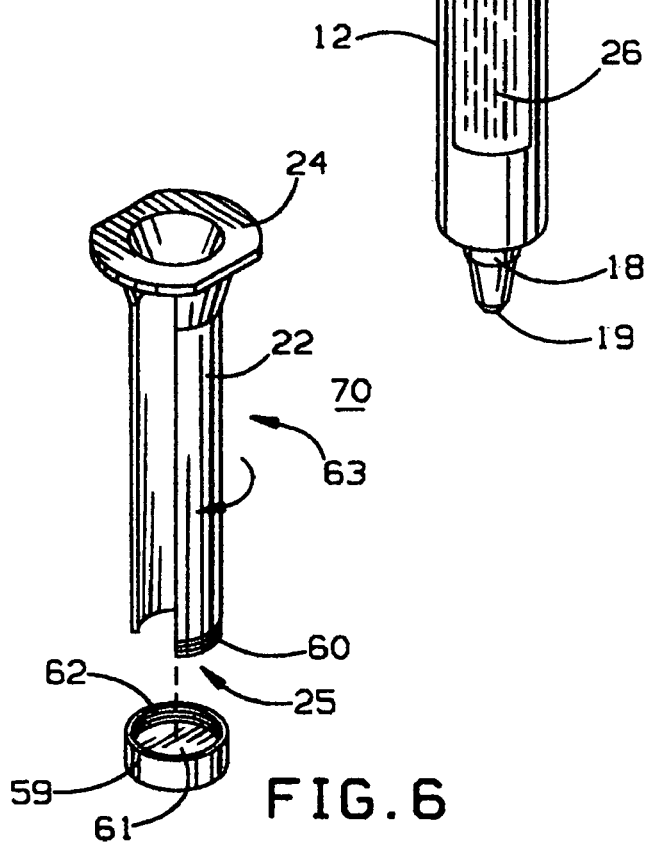
FIG. 6 is an exploded perspective view of a syringe plunger and stopper having mated threads for secure attachment to one another.

The plunger 14 shown in FIG. 1 is adapted to move the stopper 16 in only one direction in the barrel 12: toward the barrel front end 21. The plunger 14 has a blunt open end 25 for applying only forward pressure to the stopper 16 to move it toward the forward end 21 of the barrel 12 to express the syringe contents out the orifice 19 of the barrel tip 18. FIG. 6 illustrates an alternative plunger/stopper configuration 70 that can be used in the syringe 10 to move the stopper either forward or backward. This plunger/stopper configuration 70 includes a detachable plunger 63 that can move an attachable stopper 59 forward in the barrel 12 toward the front end 21 or backward toward the rear end 23 of the barrel 12.

The barrel 12 of the syringe 10 includes a rear flange 20 radially extending from the cylindrical body of the barrel 12. The rear flange 20 acts as a finger grip during use of the syringe 10.

The tip 18 extends from the forward end 21 of the barrel 12 for dispensing the contents of the barrel 12. The barrel 12 and tip 18 may be constructed in any suitable size, including standard sizes, and they are preferably sized and shaped to ease delivery of the desired medication contained in the syringe 10.

The barrel 12 can be pre-loaded with medication, preferably a liquid medicine. A mated tip cap 27 can be attached to the tip 18 to seal the orifice 19 and the stopper 16 can be pre-positioned within the barrel 12 to seal shut the barrel rear end 23. The syringe 10 can be loaded and assembled in a sterile environment and hermitically sealed in sterile packaging (not shown) to ensure delivery of a sterile syringe assembly.

A label 26 is attached to the exterior of the barrel 12 for providing information about the contents of the syringe 10, such as the name of the drug, prescription and patient information, or the like. The plunger shaft 22 can be made of a clear material so that the label 26 is viewable when the plunger 14 is attached to the barrel 12. The clear plunger shaft is an advantageous feature that greatly enhances the use of the syringe 10 because it allows the label 26 to be read without first detaching the plunger 14. However, it is noted that an opaque plunger shaft may be used as an alternative, without departing from the scope and spirit of the invention.

Figure 3:
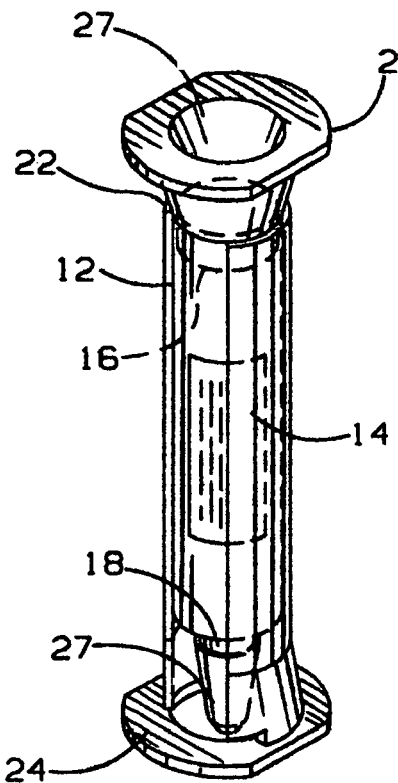
FIG. 3 is a perspective view of the syringe of FIG. 1 in its assembled, upright storage position.

The plunger 14 includes at one end a radially extending flange 24 adapted to act as a base for supporting the syringe 10 in an upright vertical position when the plunger 14 is attached to the barrel 12 (as shown in FIG. 3). The flange 24 extends radially from an end of the cylindrically-shaped shaft 22. The flange 24 also acts as thumb rest for moving the plunger 14 in the barrel 12 during use of the syringe 10.

The various components 12,14,16,27 of the syringe 10 can be constructed using any suitable material, and are preferably made using an injection-molded polymer material, such as polypropylene, HDPE, LDPE, PET or the like. The barrel 12, tip 18, and rear flange 20 are preferably a single-piece construction of molded plastic, and the plunger shaft 22 and flange 24 are likewise preferably a single-piece construction of molded plastic.

Figure 2A:
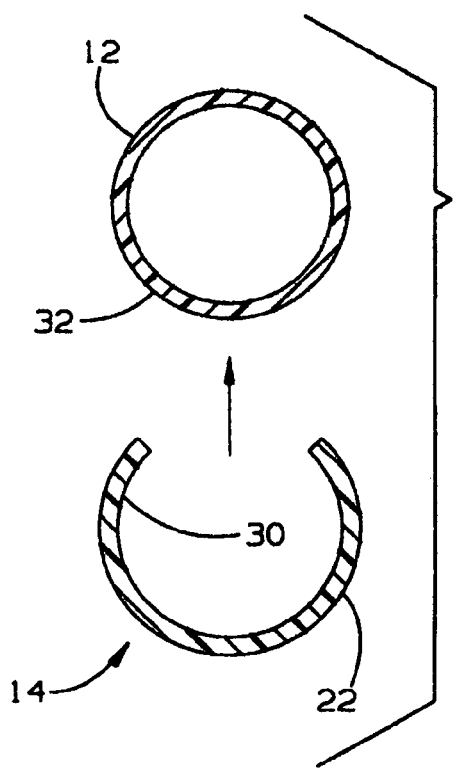
FIGS. 2A-B are cross-sectional views of the syringe of FIG. 1 along section line 2A-2A.
Figure 2B:
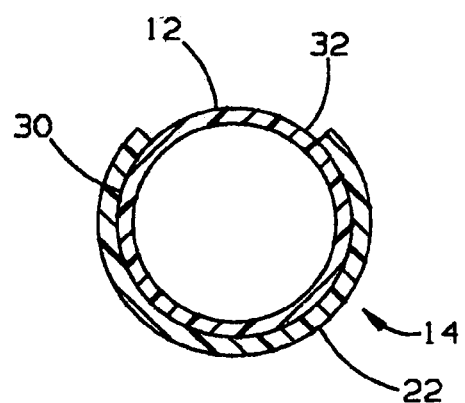

FIGS. 2A-B are cross-sectional views of the syringe 10 of FIG. 1 along section line 2A-2A. These figures clearly show the c-shaped cross-section cylindrically-shaped shaft 22. FIG. 2A shows the plunger 14 in a detached position, removed from the barrel 12. The shaft 22 has an interior surface 30 sized and shaped for snuggly engaging at least a portion of the exterior surface 32 of the cylindrical barrel 12 to securely attach the plunger 14 to the barrel 12 for storage purposes, as shown in FIG. 2B. The walls of the shaft 22 are thin enough so that they easily flex to clasp and disengage the barrel exterior, and also, so that they easily flex inwardly toward the central axis of the shaft 22 so that the shaft 22 readily fits into the rear opening 27 of the barrel 12 for applying force to the stopper 16 to move the stopper 16 in the barrel 12.

In attaching the plunger 14 to the barrel 12, the open end 25 of the shaft 22 can be aligned with the forward end 21 of the barrel 12, and then the plunger 14 can be slid down and over the length of the barrel 12 from the front. Alternatively, the plunger 14 and barrel 12 can be placed side-by-side and the barrel 12 can be pressed directly into the c-opening of the shaft 22. Reverse movements are used to detach the plunger 14 from the barrel 12. The c-shaped shaft 22 can be designed and structured (by choosing the desired shaft wall thickness and/or height) to accommodate either one or both of these attachment/detachment movements.

Although the plunger 14 described here uses a c-shaped structure to attach to the barrel 12 in a clip-on fashion, the plunger 14 may incorporate any other suitable mechanism for mounting to the barrel 12, such as an adhesive, adhesive tape, alternative mounting structure, or the like. Also, the plunger 14 can assume shapes and forms other than the c-shaped cylinder described herein in detail, yet remain fully within the spirit and scope of the invention.

FIG. 3 is a perspective view of the syringe of FIG. 1 in its assembled, upright storage position.

FIG. 4 is a perspective view of the syringe of FIG. 1 during use. In use, the plunger 14 is removed from the syringe barrel 12 and the open end 25 of the plunger shaft 22 is inserted into the rear end opening 27 of the barrel 12. The plunger 14 is then moved inside the barrel 12 (thereby moving the stopper 16) by applying pressure to the flange 20 or pulling back on the plunger 14.

Figure 5:
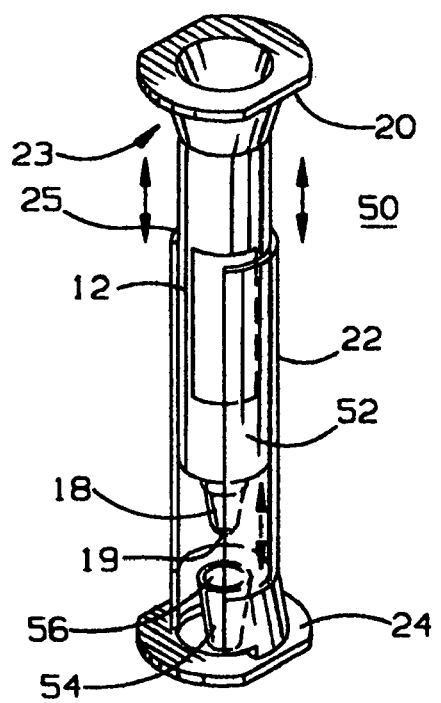
FIG. 5 is a perspective view of a syringe where the plunger includes an optional integrally formed tip cap.

FIG. 5 is a perspective view of a syringe 50, where the plunger 52 includes an optional integrally formed tip cap 54 for sealing the orifice 19 of the tip 18. The tip cap 54 is formed at one end of the plunger 52 and includes a mated cavity 56 for receiving and covering the tip 18 when the plunger 52 is attached to the cylindrical barrel 12. In attaching the plunger 52 to the barrel 12, the shaft 22 is first attached to the barrel 12 with the tip cap 54 slightly in front of the tip 18. The plunger 52 is then slid down the length of the barrel 12 toward the rear end 23 of the barrel 12 so that the tip 18 is received in the cap cavity 56.

The plunger 52 can be constructed using any suitable material, and is preferably made using an injection-molded polymer material, such as polypropylene, HDPE, LDPE, PET or the like.

FIG. 6 is an exploded perspective view of a plunger assembly 70 having a syringe plunger 63 and an attachable stopper 59 having mated threads 60,62 for secure attachment to one another. The plunger assembly 70 is a means for securely attaching one end of the plunger 63 to the stopper 59 so that the stopper 59 can be pulled back in the cylindrical barrel 12. The plunger assembly 70 can be used in syringes 10,50 to achieve both forward and backward movement of the stopper 59 within the syringe barrel 12. The plunger threads 60 are formed on the exterior surface at the open end of the plunger shaft 22. The stopper threads 62 are formed on the interior upright walls of a cavity 61 formed inside the back of the stopper 59. Screwing the plunger 63 into the stopper 59 provides a means for securely attaching one end of the plunger 63 to the stopper 59 so that the stopper 59 can be pulled back in the syringe barrel 12. The stopper 59 can be pre-positioned within the barrel 12 prior to the two pieces 59,63 being screwed together.

Other structures can be used as a means to securely attach the plunger to the stopper during use, such as a hook and loop combination, where a hook is formed in the back of the stopper and a loop for engaging the hook is formed at the open end of the plunger shaft (or visa versa).

The attachable plunger 63 and stopper 59 can be constructed using any suitable material, and are preferably made using an injection-molded polymer material, such as polypropylene, HDPE, LDPE, PET or the like.

While one or more example embodiments of the invention have been described, it will be apparent to those of ordinary skill in the art that many more embodiments are possible that are within the scope of this invention. For example, in addition to oral syringes, features of the invention can be applied to other types of syringes, such as hypodermic syringes. Further, the foregoing detailed description and drawings are considered as illustrative only of the principles of the invention. Since other modifications and changes may be or become apparent to those skilled in the art, the invention is not limited the exact construction and operation shown and described, and accordingly, all suitable modifications and equivalents are deemed to fall within the scope of the invention.

What is claimed is:

1. A syringe, comprising:
   a cylindrical barrel having an unflared portion with interior and exterior diameters, a forward end and a rear end, the cylindrical barrel also including a flared portion having a first end with the interior diameter, the first end located forward of the rear end of the barrel, and a second end opening at the rear end of the barrel with an interior diameter greater than the exterior diameter of the unflared portion of barrel;
   a tip extending from the forward end of the cylindrical barrel and having an opening smaller than the diameter of the barrel;
   a stopper movable within the barrel;
   a plunger having a resilient cylindrically-shaped shaft with a c-shaped cross-section for allowing the plunger to be clipped onto the barrel by aligning the barrel and plunger side-by-side and then pushing the plunger from the side over the exterior of the barrel, the cylindrically-shaped shaft having an interior surface sized and shaped to securely engage at least a portion of the exterior surface of the cylindrical barrel so that the plunger securely attaches to the barrel when the syringe is not in use, and the cylindrically-shaped shaft also being adapted to insert into the rear end of the barrel for applying pressure to the stopper to move the stopper toward the forward end of the barrel; and
   a flange extending radially from one end of the cylindrically-shaped shaft of the plunger, the flange extending beyond the circumference of the barrel and in substantial concentric alignment with the barrel when the plunger is attached to the exterior of the barrel, wherein the flange is configured to be located at the forward end of the cylindrical barrel and is configured to support the syringe in a stable, upright vertical position when the plunger is attached to the exterior of the cylindrical barrel.

2. The syringe of claim 1, wherein the syringe is an oral syringe.

3. The syringe of claim 1, wherein the flange and cylindrically-shaped shaft are a single-piece construction of molded plastic.

4. The syringe of claim 1, further comprising means for securely attaching one end of the plunger to the stopper so that the stopper can be pulled back in the cylindrical barrel.

5. The syringe of claim 1, wherein cylindrically-shaped shaft is clear.

6. The syringe of claim 5, further comprising a label attached to the exterior of the cylindrical barrel and viewable through the clear shaft when the plunger is attached to the cylindrical barrel.

7. The syringe of claim 1, wherein the plunger includes a tip cap integrally formed at one end of the plunger for covering the exterior of the tip when the plunger is attached to the exterior of the cylindrical barrel.

8. The syringe of claim 1, further comprising liquid contents contained within the cylindrical barrel.

9. The syringe of claim 1, further comprising a flange radially extending from rear end of the cylindrical barrel.

10. The syringe of claim 9, wherein the flange and cylindrical barrel are a single-piece construction of molded plastic.

11. The syringe of claim 1, wherein the flange has a hole formed therein.

12. The syringe of claim 1, wherein the one end of the cylindrically-shaped shaft is flared.

13. The syringe of claim 1, wherein the stopper is made of polypropylene and the cylindrical barrel is made of HDPE.

14. The syringe of claim 1, wherein the stopper is made of HDPE and the cylindrical barrel is made of polypropylene.

15. The syringe of claim 1, wherein the cylindrically-shaped shaft includes an open gap in its circumference extending along the length of the shaft forming a trough within the shaft for receiving the cylindrical barrel, the open gap having a circumferential width of at least one-quarter of the circumference of the shaft.

16. An oral syringe, comprising:
   a plastic cylindrical barrel having a forward end and an open rear end;
   a plastic tip integrally molded with the cylindrical barrel and extending from the forward end of the cylindrical barrel and having an opening smaller than the diameter of the barrel;
   a stopper movable within the barrel;
   a plastic plunger having a resilient cylindrically-shaped shaft with a c-shaped cross-section for allowing the plunger to be clipped onto the barrel by aligning the barrel and plunger side-by-side and then pushing the plunger from the side over exterior of the barrel, the cylindrically-shaped shaft having an interior surface sized and shaped to securely engage at least a portion of the exterior surface of the cylindrical barrel so that the plunger securely attaches to the barrel when the syringe is not in use, and the cylindrically-shaped shaft also being adapted to insert into the rear end of the barrel for applying pressure to the stopper to move the stopper toward the forward end of the barrel, the cylindrically-shaped shaft having an open gap in its circumference extending along the length of the shaft forming a trough within the shaft for receiving the cylindrical barrel, the open gap having a circumferential width of at least one-quarter of the circumference of the shaft, whereby forming the c-shaped cross-section; and
   a plastic flange integrally molded with the cylindrically-shaped shaft and extending radially from one end of the cylindrically-shaped shaft of the plunger, the flange extending beyond the circumference of the barrel and in substantial concentric alignment with the barrel when the plunger is attached to the exterior of the barrel.

17. The oral syringe of claim 16, wherein the stopper is made of polypropylene and the cylindrical barrel is made of HDPE.

18. The oral syringe of claim 16, wherein the stopper is made of HDPE and the cylindrical barrel is made of polypropylene.

19. The oral syringe of claim 16, wherein the flange is configured to be located at the forward end of the cylindrical barrel and is of sufficient width to support the syringe in an upright vertical position when the plunger is attached to the exterior of the cylindrical barrel.

* * * * *

UNITED STATES PATENT AND TRADEMARK OFFICE
CERTIFICATE OF CORRECTION

| | |
|---|---|
| PATENT NO. | : 7,972,312 B2 |
| APPLICATION NO. | : 11/103236 |
| DATED | : July 5, 2011 |
| INVENTOR(S) | : Robert Koopman |

It is certified that error appears in the above-identified patent and that said Letters Patent is hereby corrected as shown below:

Title Page, Item (54) Title: change "COMPAC SYRINGE" to --COMPACT SYRINGE--.

Signed and Sealed this
Twenty-eighth Day of February, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,972,312 B2 | Page 1 of 1 |
| APPLICATION NO. | : 11/103236 | |
| DATED | : July 5, 2011 | |
| INVENTOR(S) | : Robert Koopman | |

It is certified that error appears in the above-identified patent and that said Letters Patent is hereby corrected as shown below:

Title Page, Item (54) and at Column 1, line 1, Title: change "COMPAC SYRINGE" to --COMPACT SYRINGE--.

This certificate supersedes the Certificate of Correction issued February 28, 2012.

Signed and Sealed this
Twenty-seventh Day of March, 2012

David J. Kappos
*Director of the United States Patent and Trademark Office*